United States Patent
Weihrauch et al.

(10) Patent No.: US 6,194,613 B1
(45) Date of Patent: Feb. 27, 2001

(54) PROCESS FOR THE CONTINUOUS PREPARATION OF HYDROXYALKYLAMIDES

(75) Inventors: Thomas Weihrauch, Duelman; Klaus Behrendt; Silvia Herda, both of Herne; Rainer Elm, Marl, all of (DE)

(73) Assignee: Creanova Spezialchemie GmbH, Marl (DE)

(*) Notice: Subject to any disclaimer, the term of this patent is extended or adjusted under 35 U.S.C. 154(b) by 0 days.

(21) Appl. No.: 09/312,967

(22) Filed: May 17, 1999

(30) Foreign Application Priority Data

May 15, 1998 (DE) .............................. 198 21 883

(51) Int. Cl.$^7$ .................................. C07C 231/02
(52) U.S. Cl. .................. 564/135; 564/134; 564/136; 564/137; 564/159; 564/160
(58) Field of Search ...................................... 564/137, 134, 564/135, 136, 159, 160; 554/35, 36

(56) References Cited

U.S. PATENT DOCUMENTS 4,615,831 * 10/1986 Kanno et al. .................... 252/609
5,101,073 * 3/1992 Schlaefer ........................ 564/137

* cited by examiner

*Primary Examiner*—Shailendra Kumar
(74) *Attorney, Agent, or Firm*—Oblon, Spivak, McClelland, Maier & Neustadt, P.C.

(57) ABSTRACT

Process for the continuous preparation of hydroxyalkylamides Process for the continuous preparation of hydroxyalkylamides from carboxylic esters and alkanolamines, wherein the reaction of the starting materials is carried out in an extruder or intensive mixer by intensive mixing and brief reaction with supply of heat and simultaneous removal of the alcohol formed and the final product is then isolated.

15 Claims, No Drawings

PROCESS FOR THE CONTINUOUS PREPARATION OF HYDROXYALKYLAMIDES

BACKGROUND OF THE INVENTION

1. Field of the Invention

The invention relates to a process for the continuous preparation of hydroxyalkylamides from carboxylic esters and hydroxyalkylamines.

2. Discussion of the Background

DE-A 25 09 237 describes a process for preparing hydroxyalkylamides. In this process, esters and hydroxyalkylamines are reacted batchwise in the presence or absence of a solvent to give the end product. The reaction takes a number of hours.

The process is improved in EP-A-O 473 380. The temperature is selected so that a crystal slurry is formed during the reaction. The partial crystallization leads to yield improvements, since the undesirable formation of dimers of the target molecule, which is associated with elimination of hydroxyalkylamine, is suppressed. Here too, the reaction is carried out batchwise. The reaction time is a number of hours.

These synthetic methods practiced hitherto have various disadvantages: if the reaction is carried out in a solvent, the solvent has to be removed again afterwards.

The customary preparation requires slow dropwise addition of the hydroxyalkylamine.

The technique of working in a crystal slurry requires accurate correlation of viscosity and temperature, since excessive crystal formation reduces the yield. In addition, the discharge of the crystal slurry from the reactor and the subsequent compounding of the material are complicated.

OBJECTS OF THE INVENTION

One object of the present invention is to provide a less complicated, simple and continuous process for preparing hydroxyalkylamides which does not have the disadvantages mentioned.

SUMMARY OF THE INVENTION

It has been found that the preparation of hydroxyalkylamides can be carried out continuously in an extruder or intensive mixer with significant benefit.

DETAILED DESCRIPTION OF THE INVENTION

The invention provides a process for the continuous preparation of hydroxyalkylamides from carboxylic esters (or anhydrides) and alkanolamines, wherein the reaction of the starting materials is carried out in an extruder or intensive mixer by intensive mixing and brief reaction with supply of heat and simultaneous removal of the alcohol formed, and the final product is then isolated.

The process of the invention is in principle not restricted to any specific carboxylic esters and alkanolamines as starting materials.

An important principle of the invention process is that the starting materials are continuously heated briefly to a high temperature, e.g. in an intensive kneader, a singlescrew or multiscrew extruder, planetary-gear extruder, in particular a twinscrew extruder, with the corresponding alcohol being removed under reduced pressure or by stripping with gas and the intended product subsequently being isolated. The isolation is preferably carried out by subsequent rapid cooling.

It was surprising that the reaction, which requires a number of hours in the batchwise process, proceeds to a high degree of conversion in a short time. The formation of a crystal slurry of a particular viscosity, which is a difficult-to-control step in the prior art, is not necessary here. The formation of dimers can be virtually completely suppressed when the appropriate parameters are set, although high temperatures which are supposed to force dimer formation are employed at the beginning of the process.

Depending on the aim of the synthesis, it is, however, also possible to prepare products which comprise not only monomers but also additional dimers. Preparing dimers as main product is also possible.

An important aspect is the fact that brief heating in the extruder or intensive mixer at the beginning of the reaction is sufficient to react the reactants very substantially. In general, a temperature at the beginning of the reaction of at least 100° C., preferably 150° C., is required.

In a preferred embodiment of the process, the reaction is carried out in an extruder or intensive mixer having a plurality of identical or different barrel sections which can be thermally controlled independently of one another.

This is made possible by appropriate equipping of the mixing chambers or by means of the screw geometry, and also by intensive, rapid mixing with simultaneous, intensive heat exchange. This achieves uniform flow in the longitudinal direction with a very uniform residence time. Heat exchange is achieved by different temperature control in the individual barrel sections or zones of the apparatus. The temperature in the individual barrel sections is preferably 100° C.–250° C. at the beginning of the reaction and decreases from there on.

The starting materials are generally metered in in separate streams, but some of them can also be fed in together. However, it is also possible to meter in only one material stream which contains all of the starting materials. Hydroxyalkylamines or mixtures of various hydroxyalkylamines, and/or carboxylic esters and/or catalysts, and/or additives such as fluidizers and stabilizers can be combined into one starting material stream; likewise carboxylic esters, mixtures of esters and also the abovementioned additives and catalysts.

The material streams can also be divided and thus fed in in different proportions at various points on the extruder or intensive mixer. This produces targeted concentration gradients which can contribute to the completeness of the reaction.

The entry points of the starting material streams in the sequence can be varied and offset timewise.

The completeness of the reaction is ensured by removing the alcohol formed in the animation. This removal is preferably carried out by taking off the alcohols by means of reduced pressure via openings in the barrel of the extruder or intensive mixer and/or by passing a gas stream over the intensively mixed reaction mixture, in which case the more volatile alcohols are carried out by the gas stream.

The reaction can be accelerated by means of catalysts. Suitable catalysts are hydroxides and/or alkoxides of alkali metals, e.g. sodium or potassium hydroxide, sodium or potassium ethoxide, quaternary ammonium hydroxides, alkoxides and/or other strong bases. The concentration is from 0.01 to 5%, preferably from 0.1 to 1%, based on the carboxylic ester used.

Vacuum domes or gas passing-over points can be arranged in various ways and depend on the type of starting materials and on the alcohols formed. An additional point for removing residual alcohol downstream of the actual reaction section is also possible.

The preferably rapid, intensive cooling which is carried out after the rapid reaction can be integrated into the reaction section in the form of a multizone embodiment as in the case of extruders or Conterna machines. It is also possible to use: shell-and-tube heat exchangers, pipe loops, cooling rollers, air conveyors and metal conveyor belts.

Depending on its viscosity, the final product is first brought to a suitable temperature by further cooling by means of appropriate, abovementioned apparatuses and is then pelletized or comminuted to a desired particle size by means of crushing rolls, a pin mill, a hammer mill, flaking rolls or the like.

A preferred embodiment of the invention is a process for the continuous preparation of hydroxyalkylamides of the formula 1 from carboxylic esters and alkanolamines

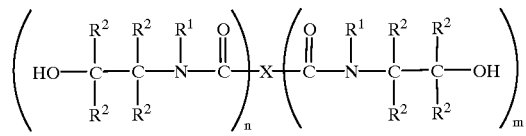

formula 1 where the substituents have the following meanings:

X: a bond, hydrogen when m=0, an alkyl, aryl, alkenyl, alkoxycarbonyl or carboxyalkenyl radical having 1–24 carbon atoms or these heteroatom-substituted radicals;

$R^1$: hydrogen, an alkyl, alkenyl, aryl or aralkyl radical having 1–24 carbon atoms, these heteroatom-substituted radicals or

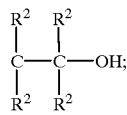

$R^2$: independently of one another, identical or different radicals selected from the group consisting of hydrogen, alkyl, aryl, aralkyl and alkenyl radicals having 1–24 carbon atoms and these heteroatom-substituted radicals; n: integer from 1 to 10;

m: integer from 0 to 2.

The process is particularly suitable for preparing

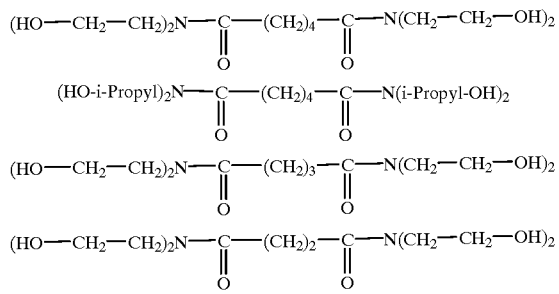

EXAMPLES

General Preparative Procedure

The carboxylic ester is fed into the feed zone of a twin-screw extruder at a temperature of from 25 to 220° C.

and the hydroxyalkylamine is metered in simultaneously at a temperature of from 25 to 200° C. One of the two streams comprises the dissolved catalyst. If required (insufficient conversion), one of the two streams can be split. This stream is metered in such that the major part (over 50%) is metered into the feed zone while the smaller stream is fed into one of the following zones so as to make an after-reaction possible.

The extruder used is composed of different barrel sections; usually, at least half can be thermally controlled.

In the case of an extruder having 8 zones, the temperatures are set as follows:

Z1: 100–220° C., Z2 to Z6: 80–220° C., Z7, Z8: 60–160° C.

If a feed stream is divided, the temperature of the second feed point is made the same or similar as in Z1.

Two zones after Z1 are provided with superimposed vacuum domes for taking off the alcohol formed during the reaction.

All temperatures are set temperatures; the temperature in the kneader barrels is set by means of electrical heating and water or air cooling (pneumatic).

The rotation rate of the twin screw, which is made up of feed and kneading elements over its entire length, is from 10 to 380 rpm.

The ratio of ester groups to hydroxyalkylamine molecules is 1:0.5–1.5, preferably 1:1.

The reaction product is either cooled and subsequently comminuted or shaped and packed.

Amide Ester (ADE) from the Reaction of Dimethyl Adipate (DMA) with Diethanolamine (DEA).

Two mol of DEA are reacted per mol of DMA. The catalyst employed is KOH (0.2% based on the amount of DMA).

Stream 1 consists of DMA and stream 2 comprises DEA in which the KOH is dissolved. The streams are not divided. They are added in the first zone of a twin-screw extruder. The methanol formed is largely extracted at two vacuum domes. The product formed is applied to a cooling belt. The residence time in the extruder is less than one minute. Composition of the product according to $^{13}$C-NMR:

| DEA | 2.0% |
|---|---|
| ADE | 97.5% |
| CH$_3$OH | 0.5% |

German patent application 19821883.4 is incorporated herein by reference.

Basically, all carboxylic acid esters and hydroxyalkyl amines are suitable and can be used in the invention process for the production of hydroxyalkyl amides.

The esters of the following dicarboxylic acids are preferred:
Butane diacid
Pentane diacid
Hexane diacid
Heptane diacid
Octane diacid
Nonane diacid
Decane diacid
Undecane diacid
Dodecane diacid.

Fundamentally, the ester groups can consist of any desired radicals. Alkyl radicals with 1–8 carbon atoms are preferred. Dimethyl and diethyl ester are especially preferred.

The following esters are preferred:
Adipinic acid dimethyl ester
Glutaric acid dimethyl ester
Succinic acid dimethyl ester.

The following amines are preferred:
Diethanol amine
N-methyl ethanol amine
Diisopropanol amine
N-methyl isopropanol amine
N-ethyl ethanol amine
2-(isopropyl)aminoethanol
2-(tert.-butyl)aminoethanol.

The following amines are especially preferred:
Diethanol amine
Diisopropanol amine.

Reaction times are dependent on the substances used and the extruder parameters (temperature, superstructure, etc.). They generally range from a time span of 30 seconds to 60 minutes, preferably 1–10 minutes, and are determinable by those of ordinary skill.

In Formula I, the radicals X as mentioned can also contain hetero-atoms, such as nitrogen, oxygen, or sulfur, and thus become these heteroatom-substituted X radicals.

Obviously, numerous modifications and variations of the present invention are possible in light of the above teachings. It is therefore to be understood that within the scope of the appended claims, the invention may be practiced otherwise than as specifically described herein.

What is claimed is:

1. A process for the continuous preparation of an hydroxyalkylamide from a carboxylic ester and an alkanolamine wherein the reaction of said carboxylic ester and alkanolamine is carried out in an extruder or intensive mixer by intensive mixing with supply of heat and simultaneous removal of the alcohol formed, and the final product is isolated.

2. The process as claimed in claim 1, wherein the reaction is carried out without solvent.

3. The process as claimed in claim 1, wherein the reaction is carried out in a single-screw, multiscrew or planetary-gear extruder.

4. The process as claimed in claim 3, wherein the reaction is carried out in a twin-screw extruder.

5. The process as claimed in claim 1, wherein the reaction is carried out in an intensive kneader or static mixer.

6. The process as claimed in claim 1, wherein the reaction is carried out in the presence of catalysts and/or additives.

7. The process as claimed in claim 1, wherein the reaction is carried out in an extruder or intensive mixer having a plurality of identical or different barrel sections which can be thermally controlled independently of one another.

8. The process as claimed in claim 7, wherein the temperature at the beginning of the reaction is at least from 100° C. to 250° C. and decreases thereafter.

9. The process as claimed in claim 1, wherein the starting materials and/or additives are introduced individually or in combination.

10. The process as claimed in claim 1, wherein alcohol formed by reaction is removed by means of reduced pressure and/or by passing an inert gas stream over the intensively mixed reaction mixture.

11. The process as claimed in claim 1, wherein the final product is obtained by rapid intensive cooling.

12. The process as claimed in claim 1, wherein said final product is a hydroxyalkylamide of the formula 1:

formula 1

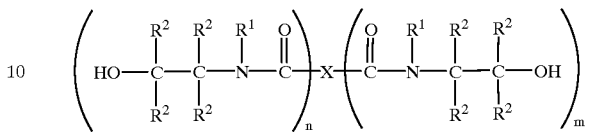

where the substituents have the following meanings:

X: a bond, hydrogen when m=0, an alkyl, aryl, alkenyl, alkoxycarbonyl or carboxyalkenyl radical having 1–24 carbon atoms or these heteroatom-substituted radicals;

$R^1$: hydrogen, an alkyl, alkenyl, aryl or aralkyl radical having 1–24 carbon atoms, these heteroatom-substituted radicals or

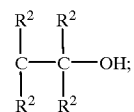

$R^2$: independently of one another, identical or different radicals selected from the group consisting of hydrogen, alkyl, aryl, aralkyl and alkenyl radicals having 1–24 carbon atoms and these heteroatom-substituted radicals;

n: integer from 1 to 10;

m: integer from 0 to 2.

13. A process as claimed in claim 1, wherein said final product is one of the following compounds:

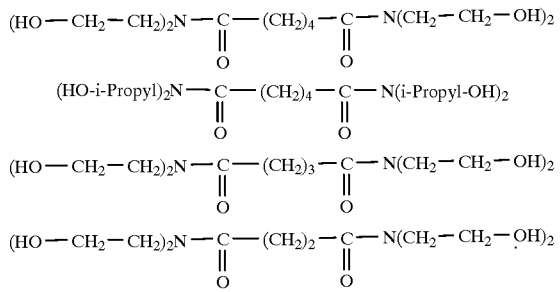

14. The process as claimed in claim 1, wherein the reaction of said carboxylic ester and alkanolamine is carried out in an extruder or intensive mixer by intensive mixing for less than one minute, and said final product is at least 97.5% hydroxyalkylamide.

15. The process as claimed in claim 1, wherein the reaction of said carboxylic acid and alkanolamine is carried out in an extruder or intensive mixer by intensive mixing for from 1 to 10 minutes.

* * * * *